United States Patent [19]
Lu

[11] Patent Number: 5,096,296
[45] Date of Patent: Mar. 17, 1992

[54] METHOD FOR MEASURING OPTICAL PATH DIFFERENCE OF AN IMBALANCED INTERFEROMETER IN A SYSTEM

[75] Inventor: Zhuo-Jun Lu, Pierrefonds, Canada

[73] Assignee: Canadian Marconi Company, Montreal, Canada

[21] Appl. No.: 557,617

[22] Filed: Jul. 24, 1990

[51] Int. Cl.[5] .................................................. G01B 9/02
[52] U.S. Cl. ................................... 356/349; 356/358; 356/363
[58] Field of Search .................... 356/349, 358, 363

[56] References Cited

U.S. PATENT DOCUMENTS

| | | |
|---|---|---|
| 4,552,457 | 11/1985 | Giallorenzi et al. |
| 4,594,003 | 6/1986 | Sommargren |
| 4,759,628 | 7/1988 | Tatsuno et al. ............. 356/349 |
| 4,874,244 | 10/1989 | Kersey |
| 4,973,153 | 11/1990 | Yokokura et al. ........... 356/358 |

Primary Examiner—Samuel Turner
Assistant Examiner—Richard E. Kurtz, II
Attorney, Agent, or Firm—Fishman, Dionne & Cantor

[57] ABSTRACT

A characteristic matrix $S(j,i)$ of the system is preformed such that each row $j$ is preformed at a predetermined constant optical path difference. Light from a laser is transmitted through the system at n different laser wavelengths, and a different datum is obtained at each wavelength whereby to obtain a set of n different data. A vector is formed from the n different data, and the characteristic matrix is multiplied by the vector to obtain a correlation vector. The maximum amplitude element of the correlation vector points to the row of a matrix which has the greatest correlation with the obtained data, so that the predetermined optical path difference of that row indicates the phase of the interferometer of the system. In a separate embodiment, the data vector is divided by the characteristic matrix to obtain a second matrix, and the second matrix is used to form an absolute deviation vector. In this method, the minimum value of the vector points to the row of the characteristic matrix which has least absolute deviation from the obtained data than any other one of the rows so that the predetermined optical path difference of this row is indicative of the phase of the interferometer. In a third embodiment, two sets of data are obtained at two different wavelengths whereby to obtain the optical path difference of the interferometer without ambiguity.

12 Claims, 3 Drawing Sheets

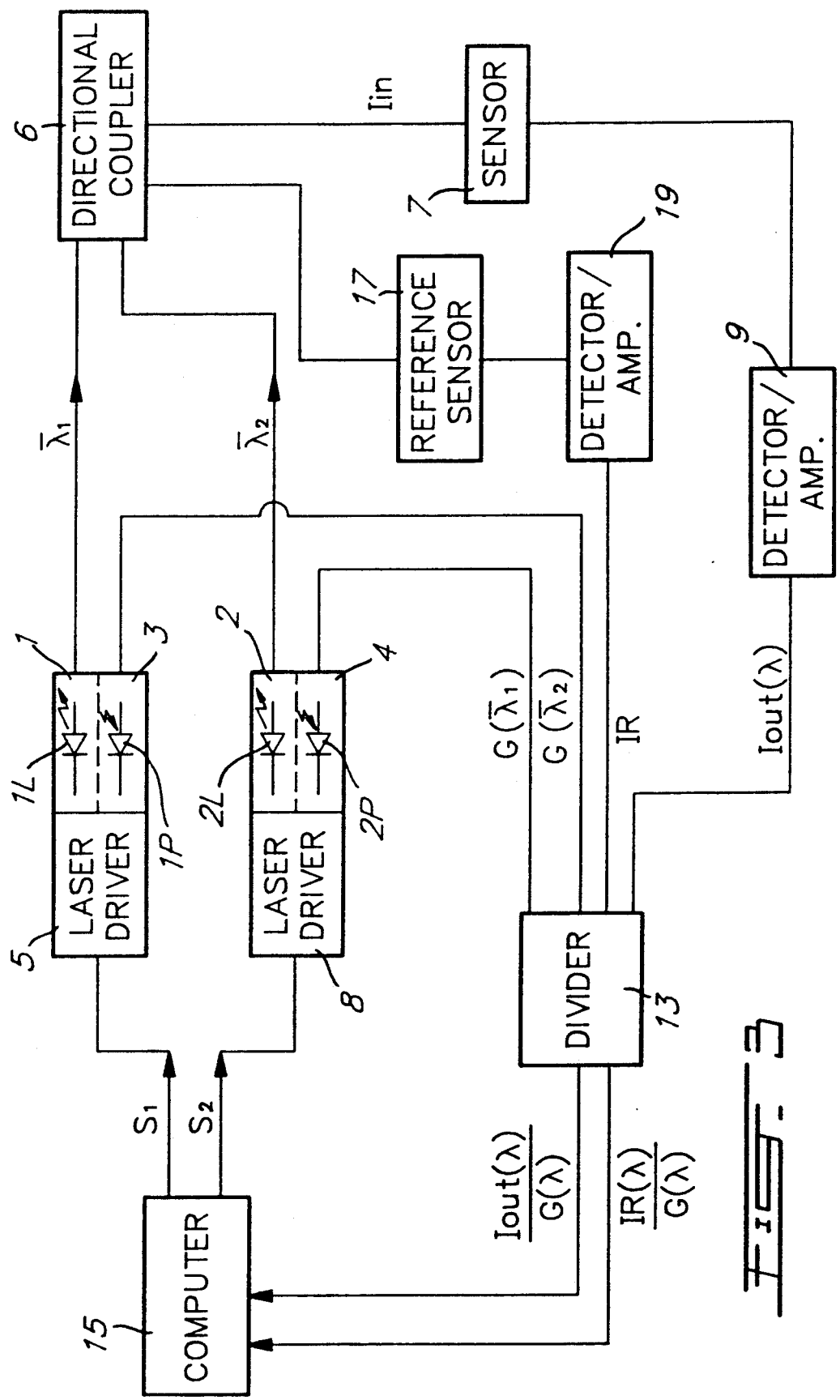

METHOD FOR MEASURING OPTICAL PATH DIFFERENCE OF AN IMBALANCED INTERFEROMETER IN A SYSTEM

BACKGROUND OF INVENTION

1. Field of the Invention

The invention relates to methods for measuring the optical path difference of an imbalanced interferometer using a wavelength modulated laser. The invention also relates to a system for carrying out the method.

2. Description of Prior Art

In my co-pending U.S. application Ser. No. 499,798, filed Mar. 27, 1990, I describe a method and system for measuring the optical path difference of an imbalanced interferometer using a wavelength modulated laser wherein the frequency of the optical fringes generated by modulating the wavelength of the laser is measured to determine the optical path difference. To carry out the method in the application, it is necessary to have a laser which can be tuned through a wide range of wavelengths without mode hopping. Such lasers are expensive which presents some restrictions in the commercial implementation of the invention of the application.

Other interferometric measurement systems are also known in the art as illustrated in, for example. U.S. Pat. No. 4,874,244, Kersey, Oct. 17, 1989, U.S. Pat. No. 4,552,457, Giallorenzi et al, Nov. 12, 1985, and U.S. Pat. No. 4,594,003, Sommargren, June 10, 1986.

The '244 patent uses two lasers 4 and 5 (see FIG. 1) operating at different wavelengths $\lambda_1$ and $\lambda_2$. The signals from the two lasers are combined in couplers 6 and 7, and the combined signal is introduced to an interferometric optical fiber system. An output of the interferometric optical fiber system is detected and divided into portions attributable to $\lambda_1$ and $\lambda_2$, and the phase lag between the output signals is measured. Lasers 4 and 5 may be modulated with signals $f_1$ and $f_2$.

As seen in the system diagram illustrated in FIG. 4 of the '457 patent, this system also uses two lasers with different wavelengths. The interferometer, as seen in FIG. 1, comprises fiber optic reference arm and difference length fiber optic sensing arm 14 and 12 respectively. The output of the interferometer is split into third and fourth beams to determine which lasers should be energized.

U.S. Pat. No. 4,594,003 teaches only a single laser 11. However, in accordance with the teachings in this patent, this laser can have its wavelength varied by current source 58.

SUMMARY OF INVENTION

It is therefore an object of the invention to provide a method for measuring the optical path difference of an imbalanced interferometer which overcomes the shortcomings of the prior art.

It is also an object of the invention to provide a system for carrying out the method.

In accordance with the broad principles of the invention, a characteristic matrix of the system is preformed. The characteristic matrix includes n columns. Each row of the matrix is formed by taking readings at n different wavelengths at a predetermined optical path difference. A set of n data readings are then taken at the same wavelengths, and a vector is formed from the set of the n data.

The matrix and vector are then mathematically manipulated to determine which row of the matrix has a greater corelationship with the set of n data than any other row. Accordingly, it is determined that the optical path difference tested is proportional to the predetermined optical path difference of the row having the greatest corelationship.

In accordance with the invention there is provided a correlation method for measuring the optical path difference $\Delta$ of an imbalanced interferometer in a system including a wavelength modulated laser, comprising:

A. preforming a characteristic matrix $S(j,i)$, of size r x n, of the system such that each row $j$ ($j=1,2,3 \ldots r$) is preformed at a predetermined constant optical path difference $\Delta_j$;

wherein
r = number of rows of the matrix
n = number of columns of the matrix

B. transmitting light from said laser through the system at n different laser wavelengths $\lambda_i$ such that;

$$2\pi \Delta_{min} \left( \frac{1}{\lambda_1} - \frac{1}{\lambda_n} \right) \geq 2\pi$$

where
$\Delta_{min}$ = minimum optical path difference of the sensor
$i = 1,2,3 \ldots n$
$\lambda_i$ is indexed so that $\lambda_i$ increases in magnitude as i increases in magnitude
each element of the characteristic matrix is expressed as $$S(j,i) = A \left( 1 + C\cos \frac{2\pi \Delta_j}{\lambda_i} \right)$$

where
A and C are constants related to the throughput and the contrast of the sensor at the wavelength of the corresponding laser;

C. obtaining a different datum at each wavelength $\lambda_i$ whereby to obtain a set of n different data;

D. forming a vector $D(i)$ from said n different data; where $$D(i) = A \left( 1 + C\cos \frac{2\pi \Delta}{\lambda_i} \right)$$

E. multiplying said characteristic matrix by said vector to obtain a correlation vector $V(j)$;

F. determining which element of the vector $V(j)$ has the largest magnitude, $V(j=j')$;

whereby it is determined that the phase $\phi$ of the sensor $$\phi = 2\pi \left( \frac{\Delta_j'}{\lambda} + k \right)$$

and $$\overline{\Delta = \Delta_j + k\overline{\lambda}}$$

where
k = a positive or negative integer $$\overline{\lambda} = \frac{1}{n} \sum_{i=1}^{n} \lambda_i.$$

In accordance with the invention there is further provided a least absolute deviation method for measuring the optical path difference $\Delta$ of an imbalanced interferometer in a system including a wavelength modulated laser, comprising:

A. preforming a characteristic matrix $S(j,i)$, of size r x n, of the system such that each row j (j=1,2,3 ... r) is preformed at a predetermined constant optical path difference $\Delta_j$;
wherein
 r = number of rows of the matrix
 n = number of columns of the matrix B. transmitting light from said laser through the system at n different laser wavelengths $\lambda_i$ such that;

$$2\pi \Delta_{min} \left( \frac{1}{\lambda_1} - \frac{1}{\lambda_n} \right) \geq 2\pi$$

where
 $\Delta_{min}$ = minimum optical path difference of the sensor
 i = 1,2,3 ... n
 $\lambda_i$ is indexed so that $\lambda_i$ increases in magnitude as i increases in magnitude
 each element of the characteristic matrix is expressed as $$S(j,i) = A\left(1 + C\cos\frac{2\pi\Delta_j}{\lambda_i}\right)$$

where
 A and C are constants related to the throughput and the contrast of the sensor at the wavelength of the corresponding laser;

C. obtaining a different datum at each wavelength $\lambda_i$ whereby to obtain a set of n different data;

D. forming a vector $D(i)$ from said n different data; where $$D(i) = A\left(1 + C\cos\frac{2\pi\Delta}{\lambda_i}\right)$$

E. dividing said vector by each row of said characteristic matrix to obtain a second matrix $A(j,i)$;

F. forming an absolute deviation vector $E(j)$ using the relationship:

$$E(j) = \frac{\sum\limits_{i}^{\overline{n}_1} \left| A(j,i) - \frac{1}{\overline{n}_1} \sum\limits_{i}^{\overline{n}_1} A(j,i) \right|}{\sum\limits_{i}^{\overline{n}_1} A(j,i)}$$

wherein
 $\overline{n}_1$ = number of readings in the data set which satisfy the condition:

$$|S(j,i) - A| = \left| AC\cos\frac{2\pi\Delta_j}{\lambda_i} \right| < a_{th}AC$$

wherein
 $a_{th}$ is a threshold value such that $0 < a_{th} < 1$;

G. determining which element of the vector $E(j)$ has the smallest magnitude $E(j=j')$;
whereby, it is determined that $$\Delta = \Delta_{j'} + k\overline{\lambda}$$

In accordance with the invention there is still further provided a method for measuring the optical path difference $\Delta$ of an imbalanced interferometer whose range is defined by $\Delta_o - K\overline{\lambda}_1 \leq \Delta \leq \Delta_o + K\overline{\lambda}_1$, using a system including a wavelength modulated laser which emits light at two center wavelengths $\overline{\lambda}_1$ and $\overline{\lambda}_2$, comprising:

A. preforming a first characteristic matrix $S_1(j,i)$, of size r x $n_1$, for the system such that each row j (j=1,2,3 ... r) is preformed at a predetermined constant optical path difference $\Delta_j$;
wherein
 r = number of rows of the matrix
 $n_1$ = number of columns of the matrix B. transmitting light from said laser through the system at $n_1$ different laser wavelengths $\lambda_{li}$ such that;

$$2\pi \Delta_{min} \left( \frac{1}{\lambda_{11}} - \frac{1}{\lambda_{n1}} \right) \geq 2\pi$$

where
 $\Delta_{min}$ = minimum optical path difference of the sensor
 i = 1,2,3 ... $n_1$
 $\lambda_{li}$ is indexed so that $\lambda_{li}$ increases in magnitude as i increases in magnitude
 each element of the characteristic matrix is expressed as $$S_1(j,i) = A\left(1 + C\cos\frac{2\pi\Delta_j}{\lambda_{1i}}\right)$$

where
 A and C are constants related to the throughput and the contrast of the sensor at the wavelength of the corresponding laser;

C. obtaining a different datum at each wavelength $\lambda_{li}$ whereby to obtain a set of $n_1$ different data;

D. forming a vector $D_1(i)$ from said $n_1$ different data; where $$D_1(i) = A_1\left(1 + C_1\cos\frac{2\pi\Delta}{\lambda_{1i}}\right)$$

and then either
 E1. multiplying said characteristic matrix by said vector to obtain a correlation vector $V_1(j)$;
 F1. determining which element of the vector $V_1(j)$ has the largest magnitude, $V_1(j=j')$; or
 E2. dividing said vector by each row of characteristic matrix to obtain a second matrix $A_1(j,i)$;
 F2. forming an absolute deviation vector $E(j)$ using the relationship:

$$E_1(j) = \frac{\sum\limits_{i}^{\bar{n}_1} \left| A_1(j,i) - \frac{1}{n_1} \sum\limits_{i}^{\bar{n}_1} A_1(j,i) \right|}{\sum\limits_{i}^{\bar{n}_1} A_1(j,i)}$$

wherein $\bar{n}_1$ = number of readings in the data set which satisfy the condition:

$$|S_1(j,i) - A| = \left| AC\cos\frac{2\pi\Delta_j}{\lambda_{1i}} \right| < a_{th} AC$$

wherein $a_{th}$ is a threshold value such that $0 < a_{th} < 1$;

F2.1 determining which element of the vector $E_1(j)$ has the smallest magnitude, $E_1(j=j')$; or E1. multiplying said characteristic matrix by said vector to obtain a correlation vector $V_1(j)$;

F1. determining which element of the vector $V_1(j)$ has the largest magnitude, $V_1(j=J')$;

to determine approximate values for $\Delta' = \Delta_{j'}$ and then:

E2. dividing said vector by each row, within the neighbourhood of $J'$ such that $J' - r' \leq j \leq J' + r'$ where $r' < r$, of said characteristic matrix to obtain a second matrix $A_1(j,i)$;

F2. forming an absolute deviation vector $E_1(j)$ using the relationship:

$$E_1(j) = \frac{\sum\limits_{i}^{\bar{n}_1} \left| A_1(j,i) - \frac{1}{n_1} \sum\limits_{i}^{\bar{n}_1} A_1(j,i) \right|}{\sum\limits_{i}^{\bar{n}_1} A_1(j,i)}$$

wherein $\bar{n}_1$ = number of readings in the data set which satisfy the condition:

$$|S_1(j,i) - A| = \left| AC\cos\frac{2\pi\Delta_j}{\lambda_i} \right| < a_{th} AC$$

wherein $a_{th}$ is a threshold value such that $0 < a_{th} < 1$;

F2.1 determining which element of the vector $E_1(j)$ has the smallest magnitude, $E(j=j')$;

whereby to determine more accurate value for $\Delta' = \Delta_{j'}$;

whereby it is determined that the phase of the sensor $$\phi' = 2\pi \left( \frac{\Delta_{j'}}{\lambda_1} + k_1 \right)$$

and $$\Delta' = \Delta_{j'} + k_1 \bar{\lambda}_1 \quad (i)$$

where $k_1$ is an integer such that $|k_1| \leq K$ $$\bar{\lambda}_1 = \frac{1}{n_1} \sum\limits_{i=1}^{n_1} \lambda_{1i}$$

$j'$ = the index such that (a) $V_1(j=j')$ is the maximum element in the correlation vector, or, (b) $E_1(j=j')$ is the minimum element in the absolute deviation vector $E_1(j)$ G. preforming a second characteristic matrix $S_2(j,i)$, of size $r \times n_2$, for the system such that each row $j$ ($j = 1,2,3 \ldots r$) is preformed at the same predetermined constant optical path difference $\Delta_j$ as in A. above;

H. transmitting light from said laser through the system at $n_2$ different laser wavelengths $\lambda_{2i}$ such that;

$$2\pi\Delta_{min}\left( \frac{1}{\lambda_{21}} - \frac{1}{\lambda_{2n_2}} \right) \geq 2\pi$$

where $\Delta_{min}$ = minimum optical path difference of the sensor $i = 1,2,3 \ldots n_2$ $\lambda_{2i}$ is indexed so that $\lambda_{2i}$ increases in magnitude as $i$ increases in magnitude each element of the characteristic matrix is expressed as $$S_2(j,i) = A\left( 1 + C\cos\frac{2\pi\Delta_j}{\lambda_{2i}} \right)$$

where

A and C are constants related to the throughput and the contrast of the sensor at the wavelength of the corresponding laser;

I. obtaining a different datum at each wavelength $\lambda_{2i}$ whereby to obtain a set of $n_2$ different data;

J. forming a vector $D_2(i)$ from said $n_2$ different data; where $$D_2(i) = A_2\left( 1 + C_2\cos\frac{2\pi\Delta}{\lambda_{2i}} \right)$$

and then either

K1. multiplying said characteristic matrix by said vector to obtain a correlation vector $V_2(j)$;

L1. determining which element of the vector $V_2(j)$ has the largest magnitude, $V_2(j=J'')$; or K2. dividing each vector by each row of said characteristic matrix to obtain a second matrix $A_2(j,i)$;

L2. forming an absolute deviation vector $E_2(j)$ using the relationship:

$$E_2(j) = \frac{\sum\limits_{i}^{\bar{n}_2} \left| A_2(j,i) - \frac{1}{n_2} \sum\limits_{i}^{\bar{n}_2} A_2(j,i) \right|}{\sum\limits_{i}^{\bar{n}_2} A_2(j,i)}$$

wherein $\bar{n}_2$ = number of readings in the data set which satisfy the condition:

$$|S_2(j,i) - A| = \left| AC\cos\frac{2\pi\Delta_j}{\lambda_{2i}} \right| < a_{th}AC$$

wherein $a_{th}$ is a threshold value such that $0 < a_{th} < 1$;

L2.1 determining which element of the vector $E_2$ has the smallest magnitude, $E_2(j=j'')$; or K1. multiplying said characteristic matrix by said vector to obtain a correlation vector $V_2(j)$;

L1. determining which element of the vector $V_2(j)$ has the largest magnitude, $V_2(j=J'')$;

to determine approximate values for $\Delta'' = \Delta_{j''}$ and then:

K2. dividing said vector by each row, within the neighbourhood of $J''$ such that $J'' - r'' < j < J'' + r''$, where $r'' < r$, of said characteristic matrix to obtain a second matrix $A_2(j,i)$;

L2. forming an absolute deviation vector $E_2(j)$ using the relationship:

$$E_2(j) = \frac{\sum_i^{\bar{n}_2} \left| A_2(j,i) - \frac{1}{n_2}\sum_i^{\bar{n}_2} A_2(j,i) \right|}{\sum_i^{\bar{n}_2} A_2(j,i)}$$

wherein $\bar{n}_2$ = number of readings in the data set which satisfy the condition:

$$|S_2(j,i) - A| = \left| AC\cos\frac{2\pi\Delta_j}{\lambda_{2i}} \right| < a_{th}AC$$

wherein $a_{th}$ is a threshold value such that $0 < a_{th} < 1$;

L2.1 determining which element of the vector $E_2(j)$ has the smallest magnitude, $E_2(j=j'')$;

whereby to determine more accurate value for $\Delta'' = \Delta_{j''}$;

whereby it is determined that the phase of the sensor $$\phi'' = 2\pi\left(\frac{\Delta_{j''}}{\lambda_2} + k_2\right)$$

and $$\Delta'' = \Delta_{j''} + k_2\bar{\lambda}_2 \qquad \text{(ii)}$$

where
$k_2$ is an integer such that $|k_2| \leq K$ $$\bar{\lambda}_2 = \frac{1}{n_2}\sum_{i=1}^{n_2}\lambda_{2i}$$

$j''$ = the index such that (a) $V_2(j=j'')$ is the maximum element in the correlation vector, or, (b) $E_2(j=j'')$ is the minimum element in the absolute deviation vector $E_2(j)$ determining $k_1$ or $k_2$ in equations (i) or (ii) by determining the minimum $|\Delta' - \Delta''|$ among all possible values of $k_1$ and $k_2$;

whereby to obtain the optical path difference $$\Delta = \Delta_{j'} + k_1\bar{\lambda}_1 = \Delta_{j''} + k_2\bar{\lambda}_2.$$

In accordance with the invention there is still further provided a system for measuring the optical path difference $\Delta$ of an imbalanced interferometer, comprising:

at least one diode laser means having a control terminal and a laser diode and a photodiode, said laser diode having a laser diode output terminal and said photodiode having a photodiode output terminal;

laser driver means having a control terminal and an output terminal;

said imbalanced interferometer having an input terminal and an output terminal;

a detector having an input terminal and an output terminal;

processor means having input means and output means;

said output means of said processor means being electrically connected to said control terminal of said laser drive means;

said output means of said laser driver means being connected to said control terminal of said diode laser;

said output terminal of said laser diode being optically connected to said input terminal of said interferometer;

said output terminal of said interferometer being optically connected to said input terminal of said detector;

divider means having a first input terminal, a second input terminal and an output terminal;

said output terminal of said detector being electrically connected to said first input terminal of said divider means;

said output terminal of said photodiode being electrically amplified by the laser driver and connected to said second input terminal of said divider means; and said output terminal of said divider means being connected to said input means of said processor means.

BRIEF DESCRIPTION OF DRAWINGS

The invention will be better understood by an examination of the following description, together with the accompanying drawings, in which:

FIG. 3 illustrates an alternative embodiment of the inventive system.

DESCRIPTION OF PREFERRED EMBODIMENTS

Figure 1:
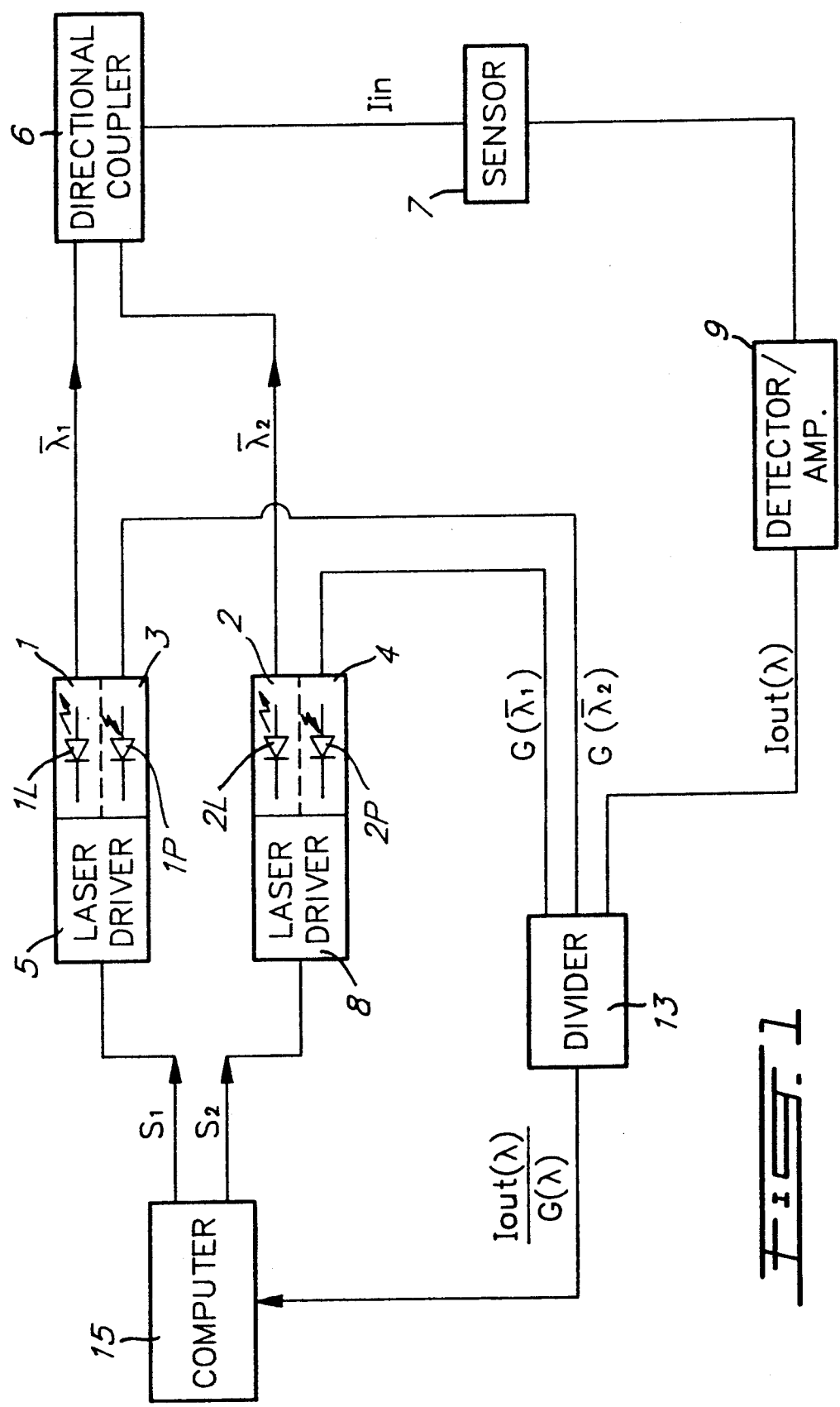
FIG. 1 illustrates one embodiment of an inventive system for implementing the inventive method.
Figure 2A:
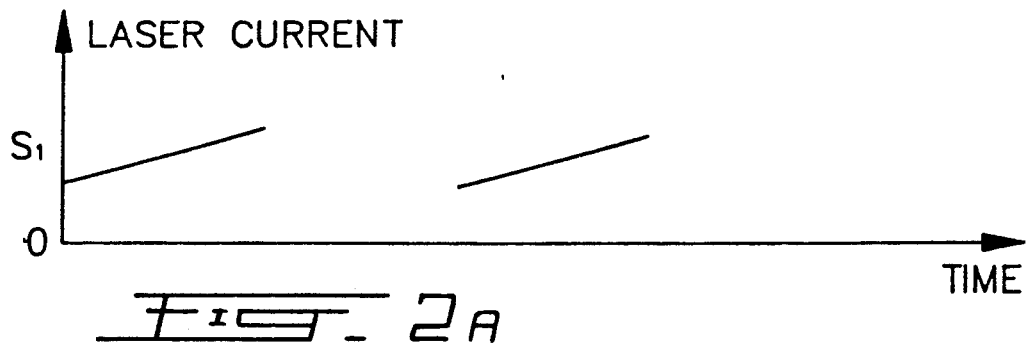
FIGS. 2A, 2B, 2C and 2D are graphs useful in understanding the invention.
Figure 2B:
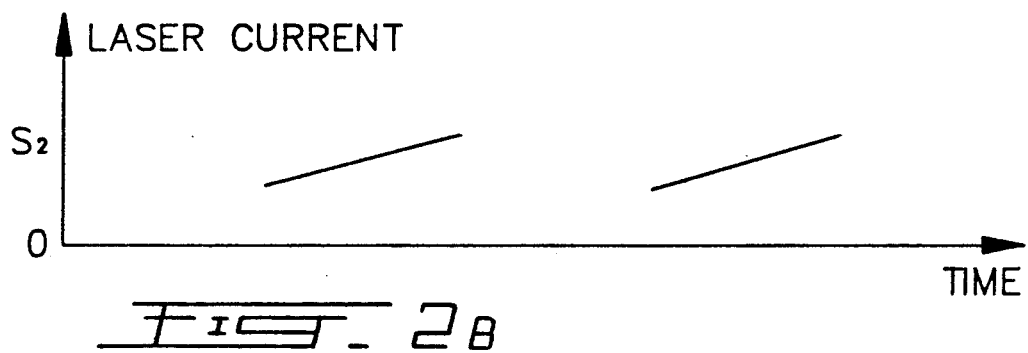
Figure 2C:
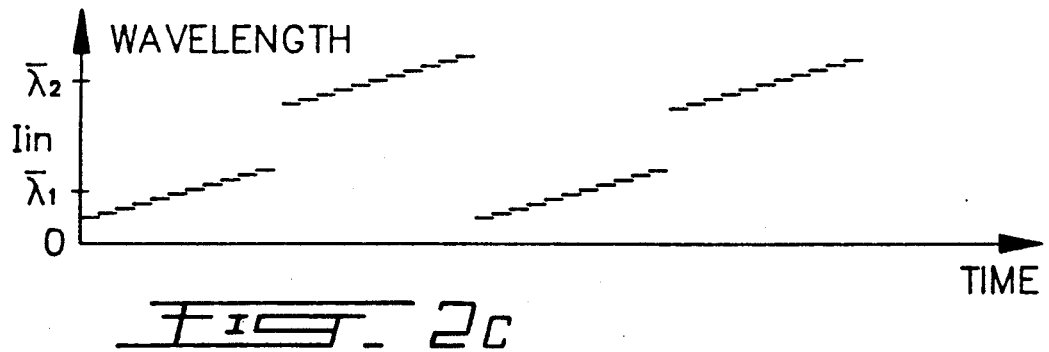
Figure 2D:
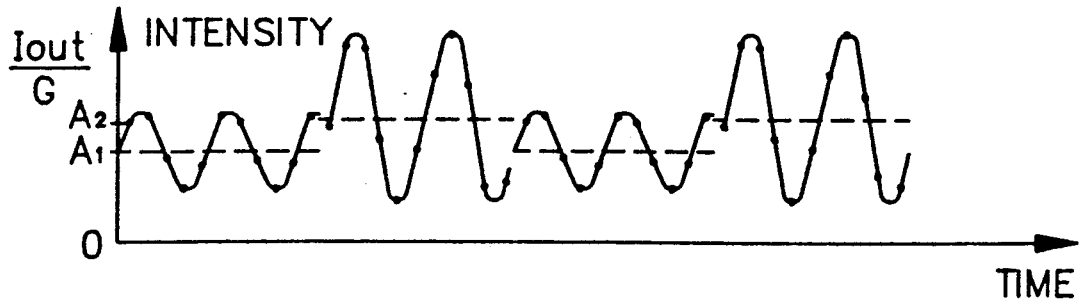

Referring to FIG. 1, the system includes two wavelength modulated diode laser means 1 and 2, each driven by a temperature stabilized laser driver 5 and 8 respectively. Each diode laser comprises a laser diode (1L and 2L) which emits light, and a photodiode (1P and 2P) which monitors the intensity variation of its associated laser diode. Preferably, the photodiode outputs are amplified by amplifier means in their associated laser drivers. Laser diode 1L has a center wavelength of 780 mn, and laser diode 2L has a center wavelength of 810 nm. It is, of course, not necessary that these particular wavelengths be used. In addition, the invention can be carried out with only a single laser as long as the laser has a width enough wavelength band. However, when a single laser cannot provide the breadth of wavelengths needed, then two separate lasers must be used.

The outputs of laser diodes 1L and 2L are optically coupled to the inputs of directional coupler 6, The output of the directional coupler 6 is optically coupled to the input of sensor 7.

The output of sensor 7 is optically connected to the input of detector 9 where the optical signal is transformed to an electrical signal. The amplified outputs of photodiodes 1P and 2P are connected to respective input terminals of divider 13.

The output of detector 9 is electrically connected to a third input terminal of divider 13, and the output of the divider 13 is electrically coupled to an input of processor 15.

Processor 15 provides control signals $S_1$ and $S_2$ to control laser drivers 5 and 8 respectively. Laser drivers 5 and 8, in turn, provide signals to control the operation of laser diodes 1L and 2L, i.e., turn them ON or OFF, adjust their frequency, etc. When both laser diodes 1L and 2L are used, only one laser will operate at a time.

Likewise, there is an optical connection between the output of sensor 7 and the input of detector 9.

The output of detector 9 constitutes electrical signals, so that the connection between the output of 9 and the third input of divider 13 and the connection between output of 13 and the input of processor 15 are electrical connections.

Turning now to FIG. 2, it can be seen that, as the laser current is increased, the wavelength at the output of the laser will also increase. However, in view of the mode hopping characteristics of the lasers, the increase will not be smooth but rather will be accomplished in steps. Although each step is shown as horizontal, there is actually a slight rise from left to right.

As is known in the art, the relationship between the input intensity and output intensity of an interferometric sensor, e.g., a MACH-ZEHNDER interferometer, which could be used as the sensor 7 in FIG. 1, can be expressed as:

$$I_{out} = \frac{1}{2} I_{in} \left( 1 + \cos \frac{2\pi\Delta}{\lambda} \right) = \frac{1}{2} I_{in}(1 + \cos\phi) \quad (1)$$

where
$I_{out}$ = output intensity of the interferometer
$I_{in}$ input intensity of the interferometer
$\phi$ = phase of the interferometer
$\lambda$ = wavelength of the laser
$\Delta$ = optical path difference.

It is also well known that, unless a very complex and expensive laser is used, it is possible to achieve only very small deviations, typically of the order of a few angstroms, of the laser wavelength before mode hopping occurs. In prior art methods and systems, very large imbalance interferometers, $\Delta > 2000\lambda$, are required. As will be seen, in the present system, only slightly imbalanced interferometers are required, $\Delta > 300\lambda$.

Using the system as illustrated in FIG. 1, it is possible to obtain data sets D(i):

$$D(i) = \frac{I_{out}(\lambda_i)}{G(\lambda_i)} \quad i = 1, 2, \ldots n \quad (2)$$

by varying the wavelength of the laser, despite mode hopping which occurs during the modulation process. Because this is a discrete method, it will work either with continuous wavelength change or discrete wavelength changes.

In the above equation, D is a data set and G is a factor determined by the gain of the laser with respect to current changes.

In view of equation (1) above, D can also be expressed as:

$$D(i) = A \left( 1 + C\cos\frac{2\pi\Delta}{\lambda_i} \right) \quad (3)$$

where A and C are constants relating to the throughput and contrast of the interferometer at the wavelength of the laser.

In accordance with the inventive method, a characteristic matrix, S(j,i) is preformed as follows:

For each jth row of the matrix, the interferometer is preset at a predetermined optical path differences $\Delta_j$. For example, if the interferometer is to be measuring temperature, then the temperature of the interferometer will be preset to known values corresponding to known optical path differences. At each predetermined optical path difference, the wavelength of the laser is varied through n different wavelengths.

Thus, the optical path difference for the jth row will be set in the interferometer, and the wavelength of the laser will be varied through the n wavelengths. Readings are taken at each of the wavelengths, in accordance with equation (2) above. The n values thus obtained will constitute the n values in the jth row.

The optical path difference is then set to a different predetermined value to calculate the data for the (j+1)th row, and the wavelength of the laser is then varied through the same n wavelengths as above. This is continued until all of the rows have been completed.

The matrix S(j,i) can be formed using the arrangement in FIG. 1 by placing the interferometer 7 in a reference mode in which the optical path difference of the interferometer 7 can be actively changed. In order to be able to recalibrate the system without disturbing the interferometer from its measurement mode, a system as illustrated in FIG. 3 can be used. As can be seen, FIG. 3 is identical to FIG. 1 except that it includes the reference interferometer 17, whose optical path difference can be actively changed, a second detector 19 and a fourth input terminal and second output terminal at divider 13. Directional coupler 6 directs the output of laser diodes 1L or 2L to sensor 7 and reference sensor 17. In the FIG. 3 embodiment, the divider has two output channels, an the two output channels of the divider 13 are connected to two input terminals of computer 15. With this arrangement, it is possible to both read data and perform a calibration either independently or simultaneously under the control of the computer 15. Thus, a new characteristic matrix can be formed whenever the system needs calibration. The interferometer 7 can be passive. No active means is required to vary the optical path difference of the sensor by the system as in the system shown in FIG. 1, and measurements from sensor 7 can be taken any time when the system is ready.

A vector is formed from these measurements. Typically, the formation of the vector will be accomplished by the processor 15.

The remainder of the steps in the correlation and least absolute deviation methods, described below, are performed by the processor.

STEP 1—CALCULATING THE PHASE OF THE INTERFEROMETER

The objective is to obtain the phases of the interferometer, as described in equation (1), at the two center wavelengths, $\lambda_1$ and $\lambda_2$, respectively.

The two methods can be used to calculate the phases. For each center wavelength, either Method I (correlation) or Method II (least absolute deviation) or the combination of both, described below may be used.

METHOD I—CORRELATION METHOD

Using the characteristics matrix and the vector D, a correlation vector is calculated as follows:

$$V(j) = \sum_{i=1}^{n} S(j,i)D(i) \qquad j = 1, 2, \ldots m \qquad (4)$$

where

S is the m x n characteristic matrix m is an integers such as that $\lambda/m$ is the fraction of a fringe the system can resolve.

The S matrix above consists of the m sets of D(i) premeasured at the center fringe of the full range of the sensor. For example, if the imbalance of the interferometer is at $\Delta_0$ and the full range of the sensor is two K fringes, i.e., $$\Delta_0 - K\overline{\lambda} \leq \Delta \leq \Delta_0 + K\overline{\lambda} \qquad (5)$$

then $$S(j,i) = D(i) \text{ measured at } \Delta_j = \Delta_0 j\overline{\lambda}/m \qquad (6)$$

where $\overline{\lambda}$ = the average wavelength around one of the center wavelengths of the modulated laser. If 780 nm and 810 nm are the center wavelengths of the laser being used, then $\overline{\lambda}$ is either approximately equal to 780 nm or 810 nm.

Since V(j) is the cross correlation with zero lag between the jth row of the S matrix and the measured data D, the maximum of V, $V(j=j')$ indicates there is a strong direct correlation between the two sets of data. This may be interpreted as indicating that the phase of the interferometer is $$\phi = 2\pi \left( \frac{j'}{m} + k \right) \qquad (7)$$

where k is an integer and $|k| \leq K$ or that the path difference of the sensor is $$\Delta = \Delta_{j'} + k\overline{\lambda} \qquad (8)$$

METHOD II—LEAST ABSOLUTE DEVIATION METHOD

Once again, the matrix S(j,i) is formed, and a data set is taken to provide a vector D(i). However, in this case, the vector is divided by the matrix to form a new matrix A(j,i). That is:

$$A(j,i) = \frac{D(i)}{S(j,i)} \qquad j = 1, 2, 3 \ldots m \qquad (9)$$

Using the above matrix, an absolute deviation vector E(j) is formed such that:

$$E(j) = \frac{\sum_{i}^{\overline{n}_1} \left| A(j,i) - \frac{1}{n_1} \sum_{i}^{\overline{n}} A(j,i) \right|}{\sum_{i}^{\overline{n}_1} A(j,i)} \qquad (10)$$

In equation (10), $\overline{n} \leq n$, and $\overline{n}$ is the number of datum in the data set which satisfy the condition:

$$|S(j,i) - A| = \left| A\cos\frac{2\pi\Delta_j}{\lambda_i} \right| < a_{th}AC \qquad (11)$$

where $a_{th}$ is a threshold value.

In accordance with the present method, the minimum of E(j) is determined. The minimum of E(j), $E(j=j')$ indicates that the j'th row of the matrix S has the least absolute deviation from the data of the vector D compared to the absolute deviation of all other rows. Accordingly, it can once again be said that $$\phi = 2\pi \left( \frac{\Delta_{j'}}{\overline{\lambda}} + k \right) \qquad (12)$$

and $$\Delta = \Delta_{j'} + k\overline{\lambda}. \qquad (13)$$

STEP 2—COMPARING THE OPTICAL PATH DIFFERENCES

To remove the ambiguity having regards to the constant k in equation (8) or equation (13), this step compares the optical path differences obtained at the two different center wavelengths.

The procedure of the first step above-described is carried out using a center wavelength, $\overline{\lambda}_1$ for example, 780 nm. This will yield the equation:

$$\Delta' = \Delta_{f} + k_1\overline{\lambda}_1 \qquad (14)$$

The procedure would then once again be used using a center wavelength 810 nm, i.e., $\overline{\lambda}_2$. This would yield the equation $$\Delta'' = \Delta_{f'} + k_2\overline{\lambda}_2 \qquad (15)$$

It is noted that for carrying out the second part of the procedure, a characteristic matrix must be formed using the second center wavelength 810 nm. The $\Delta_j$ for forming the second matrix are the same as the $\Delta_j$ used in forming the first matrix. However, obviously, the wavelengths $\lambda_{2i}$ would be different from the wavelengths $\lambda_{1i}$.

In equations (14) and (15), $j_1$ and $j_2$ are the row numbers in $S_1$ and $S_2$ respectively.

In order to determine $|k_1| \leq K$ or $|k_2| \leq K$ without ambiguity, the full range of the sensor must be limited to:

$$K \leq \frac{\bar{\lambda}_1}{2(\bar{\lambda}_2 - \bar{\lambda}_1)} \quad (16)$$

and the resolution of the system must satisfy:

$$K \frac{(\lambda_{1n1} - \lambda_{11})}{2} \leq \frac{\bar{\lambda}}{m} \quad (17)$$

and $$K \frac{(\lambda_{2n2} - \lambda_{12})}{2} \leq \frac{\bar{\lambda}_2}{m} \quad (18)$$

and $$m \geq \frac{4\bar{\lambda}_2}{(\bar{\lambda}_2 - \bar{\lambda}_1)} \quad (19)$$

In the specific embodiment, wherein $\bar{\lambda}_1$ is approximately 780 nm and $\bar{\lambda}_2$ is approximately equal to 810 nm, then m must be greater than 110 and then K must be less than or equal to 13.

Within this range, $k_1 = k_2$ or $k_1 = k_2 \pm 1$. Ideally, $\Delta' = \Delta''$. Therefore, $k_1$ or $k_2$ can be determined by searching the minimum of $|\Delta' - \Delta''|$ among all possible combinations of $k_1$ and k2.

The value for $\Delta$ can now be determined approximately equal to $\Delta'$ and is approximately equal to $\Delta''$.

Depending on the condition of the system, either Method I or Method II, as above-described in STEP I, can be used to determine either $\Delta'$ or $\Delta''$. Thus, Method I could be used to determine both $\Delta'$ and $\Delta''$, or Method II could be used to determine both $\Delta'$ and $\Delta''$. Alternatively, Method I could be used to determine $\Delta'$ and Method II could be used to determine $\Delta''$ or vice-versa.

Method I is a faster method and uses less computation time, but the accuracy of Method I relies on the fact that the mean values of each row of the S matrix remain constant. Method II requires more computation time, but is not subject to the above constraint.

Finally, Method I could be used to first determine approximate values of $\Delta'$ and $\Delta''$. Method II would then be used to determine the values of $\Delta'$ and $\Delta''$ more accurately and faster taking into account the values given with Method I. Thus, to determine $\Delta'$, Method I would first be used to obtain an approximate value of $\Delta' = \Delta_{j'}$. Method II would then be applied only to the neighbourhood of J' in the S matrix, rather than the whole S matrix, to determine a more accurate value of $\Delta' = \Delta_j$. Using the combination of the two Methods requires less computation time than using the Method II alone. $\Delta''$ would be determined in the same way.

Although several embodiments have been above described, this was for the purpose of illustrating, but not limiting, the invention. Various modifications, which will come readily to the mind of one skilled in the art, are within the scope of the invention as defined in the appended claims.

I claim:

1. A correlation method for measuring the optical path difference $\Delta$ of an imbalanced interferometer in a system including a wavelength modulated laser, comprising:
   A. preforming a characteristic matrix S(j,i), of size r x n, of the system such that each row j (j = 1,2,3 . . . r) is preformed at a predetermined constant optical path difference $\Delta_j$;

wherein
   r = number of rows of the matrix
   n = number of columns of the matrix
B. transmitting light from said laser through the system at n different laser wavelengths $\lambda_i$ such that;

$$2\pi \Delta_{min} \left( \frac{1}{\lambda_1} - \frac{1}{\lambda_n} \right) \geq 2\pi$$

where
$\Delta_{min}$ = minimum optical path difference of the sensor
i = 1,2,3, . . . n
$\lambda_i$ is indexed so that $\lambda_i$ increases in magnitude as i increases in magnitude
each element of the characteristic matrix is expressed as $$S(j,i) = A \left( 1 + C \cos \frac{2\pi \Delta_j}{\lambda_i} \right)$$

where
A and C are constants related to the throughput and the contrast of the sensor at the wavelength of the corresponding laser;
C. obtaining a different datum at each wavelength $\lambda_i$ whereby to obtain a set of n different data;
D. forming a vector D(i) from said n different data; where $$D(i) = A \left( 1 + C \cos \frac{2\pi \Delta}{\lambda_i} \right)$$

E. multiplying said characteristic matrix by said vector to obtain a correlation vector V(j);
F. determining which element of the vector V(j) has the largest magnitude, V(j=j');
whereby it is determined that the phase $\phi$ of the sensor $$\phi = 2\pi \left( \frac{\Delta_{j'}}{\bar{\lambda}} + k \right)$$

and $$\Delta = \Delta_{j'} + \bar{k}\bar{\lambda}$$

where
k = a positive or negative integer $$\bar{\lambda} = \frac{1}{n} \sum_{i=1}^{n} \lambda_i.$$

2. A method as defined in claim 1 wherein said system comprises means for detecting output light intensity $I_{out}(\lambda_i)$ of said interferometer at each of said wavelengths; and
means for detecting the gain $G(\lambda_i)$ of said laser at each of said wavelengths;
and including the step of determining the ratio $$\frac{I_{out}(\lambda_i)}{G(\lambda_i)}$$

wherein $$D(i) = \frac{I_{out}(\lambda_i)}{G(\lambda_i)}.$$

3. A method as defined in claim 2 wherein said characteristic matrix S(j,i) preformed by:
selecting r different optical path differences $\Delta_j$;
setting said interferometer to said optical path differences $\Delta_j$ one at a time;
at each jth optical path difference, transmitting light from said laser through the system at n different laser wavelengths $\lambda_i$;
whereby, the magnitude of each element S(j,i) is given by the ratio:

$$S(j,i) = \left[\frac{I_{out}(\lambda_i)}{G(\lambda_i)}\right]_j$$

4. A method as defined in claim 3 wherein r ≥ m; wherein
m is an integer; and
m is selected such that $\lambda/m$ is the fraction of a fringe the system can resolve.

5. A least absolute deviation method for measuring the optical path difference $\Delta$ of an imbalanced interferometer in a system including a wavelength modulated laser, comprising:
A. preforming a characteristic matrix S(j,i), of size r x n, of the system such that each row j (j=1,2,3 ... r) is preformed at a predetermined constant optical path difference $\Delta_j$;
wherein
r = number of rows of the matrix
n = number of columns of the matrix
B. transmitting light from said laser through the system at n different laser wavelengths $\lambda_i$ such that;

$$2\pi\Delta_{min}\left(\frac{1}{\lambda_1} - \frac{1}{\lambda_n}\right) \geq 2\pi$$

where
$\Delta_{min}$ = minimum optical path difference of the sensor
i = 1,2,3 ... n
$\lambda_i$ is indexed so that $\lambda_i$ increases in magnitude as i increases in magnitude
each element of the characteristic matrix is expressed as $$S(j,i) = A\left(1 + C\cos\frac{2\pi\Delta_j}{\lambda_i}\right)$$

where
A and C are constants related to the throughput and the contrast of the sensor at the wavelength of the corresponding laser;
C. obtaining a different datum at each wavelength whereby to obtain a set of n different data;
D. forming a vector D(i) from said n different data; where $$D(i) = A\left(1 + C\cos\frac{2\pi\Delta}{\lambda_i}\right)$$

E. dividing said vector by each row of said characteristic matrix to obtain a second matrix A(j,i);
F. forming an absolute deviation vector E(j) using the relationship:

$$E(j) = \frac{\sum_i^{\overline{n}}\left|A(j,i) - \frac{1}{\overline{n}}\sum_i^{\overline{n}}A(j,i)\right|}{\sum_i^{\overline{n}}A(j,l)}$$

wherein
$\overline{n}$ = number of readings in the data set which satisfy the condition:

$$|S(j,i) - A| = \left|A\cos\frac{2\pi\Delta_j}{\lambda_i}\right| < a_{th}AC$$

wherein
$a_{th}$ is a threshold value such that $0 < a_{th} < 1$;
G. determining which element of the vector E(j) has the smallest magnitude, E(j=j');
whereby, it is determined that $$\Delta = \Delta_{j'} + k\overline{\lambda}$$

where k = a positive or negative integer $$\overline{\lambda} = \frac{1}{n}\sum_{i=1}^{n}\lambda_i.$$

6. A method as defined in claim 5 wherein said system comprises means for detecting output light intensity $I_{out}(\lambda_i)$ of said interferometer at each of said wavelengths; and
means for detecting the gain $G(\lambda_i)$ of said laser at each of said wavelengths;
and including the step of determining the ratio $$\frac{I_{out}(\lambda_i)}{G(\lambda_i)}$$

wherein $$D(i) = \frac{I_{out}(\lambda_i)}{G(\lambda_i)}.$$

7. A method as defined in claim 6 wherein said characteristic matrix is S(j,i), and said characteristic matrix is preformed by:
selecting r different optical path differences $\Delta_j$;
setting said interferometer to said optical path differences $\Delta_j$ one at a time;
at each jth optical path difference, transmitting light from said laser through the system at n different laser wavelengths $\lambda_1$;
whereby, the magnitude of each element S(j,i) given by the ratio:

$$S(j, i) = \left[ \frac{I_{out}(\lambda_i)}{G(\lambda_i)} \right]_j .$$

8. A method as defined in claim 7 wherein $r \geq m$; wherein m is an integer; and m is selected such that $\lambda/m$ is the fraction of a fringe the system can resolve.

9. A method for measuring the optical path difference $\Delta$ of an imbalanced interferometer whose range is defined by $\Delta_o - K\overline{\lambda}_1 \leq \Delta \leq \Delta_o + K\overline{\lambda}_1$ using a system including a wavelength modulated laser which emits light at two center wavelengths $\overline{\lambda}_1$ and $\overline{\lambda}_2$, comprising:

A. preforming a first characteristic matrix $S_1(j,i)$, of size $r \times n_1$, for the system such that each row j $(j=1,2,3 \ldots r)$ is preformed at a predetermined constant optical path difference $\Delta_j$;

wherein r = number of rows of the matrix $n_1$ = number of columns of the matrix B. transmitting light from said laser through the system at $n_1$ different laser wavelengths $\lambda_{li}$ such that;

$$2\pi \Delta_{min} \left( \frac{1}{\lambda_{11}} - \frac{1}{\lambda_{1n_1}} \right) \geq 2\pi$$

where $\Delta_{min}$ = minimum optical path difference of the sensor $i = 1,2,3 \ldots n_1$ $\lambda_{li}$ is indexed so that $\lambda_{li}$ increases in magnitude as i increases in magnitude each element of the characteristic matrix is expressed as $$S_1(j,i) = A \left( 1 + C\cos \frac{2\pi \Delta_j}{\lambda_{1i}} \right)$$

where

A and C are constants related to the throughput and the contrast of the sensor at the wavelength of the corresponding laser;

C. obtaining a different datum at each wavelength $\lambda_{li}$ whereby to obtain a set of $n_1$ different data;

D. forming a vector $D_1(i)$ from said $n_1$ different data; where $$D_1(i) = A_1 \left( 1 + C_1 \cos \frac{2\pi \Delta}{\lambda_{1i}} \right)$$

and then either

E1. multiplying said characteristic matrix by said vector to obtain a correlation vector $V_1(j)$;

F1. determining which element of the vector $V_1(j)$ has the largest magnitude, $V_1(j=j')$; or E2. dividing said vector by each row of said characteristic matrix to obtain a second matrix $A_1(j,i)$;

F2. forming an absolute deviation vector $E_1(j)$ using the relationship:

$$E_1(j) = \frac{\sum_i^{\overline{n}_1} \left| A_1(j,i) - \frac{1}{\overline{n}_1} \sum_i^{\overline{n}_1} A_1(j,i) \right|}{\sum_i^{\overline{n}_1} A_1(j,i)}$$

wherein $n_1$ = number of readings in the data set which satisfy the condition:

$$|S_1(j,i) - A| = \left| AC\cos \frac{2\pi \Delta_j}{\lambda_i} \right| < a_{th} AC$$

wherein $a_{th}$ is a threshold value such that $0 < a_{th} < 1$;

F2.1 determining which element of the vector $E_1(j)$ has the smallest magnitude, $E_1(j=j')$; or E1. multiplying said characteristic matrix by said vector to obtain a correlation vector $V_1(j)$;

F1. determining which element of the vector $V_1(j)$ has the largest magnitude, $V_1(j=J')$;

to determine approximate values for $\Delta' = \Delta_{J'}$ and then:

E2. dividing each vector by each row, within the neighbourhood of J' such that $J' - r' \leq j \leq J' + r'$, where $r' < r$, of said characteristic matrix to obtain a second matrix $A_1(j,i)$;

F2. forming an absolute deviation vector $E_1(j)$ using the relationship:

$$E_1(j) = \frac{\sum_i^{\overline{n}_1} \left| A_1(j,i) - \frac{1}{\overline{n}} \sum_i^{\overline{n}_1} A_1(j,i) \right|}{\sum_i^{\overline{n}_1} A_1(j,i)}$$

wherein $n_1$ = number of readings in the data set which satisfy the condition:

$$|S_1(j,i) - A| = \left| AC\cos \frac{2\pi \Delta_j}{\lambda_i} \right| < a_{th} AC$$

wherein $a_{th}$ is a threshold value such that $0 < a_{th} < 1$;

F2.1 determining which element of the vector $E_1(j)$ has the smallest magnitude, $E(j=j')$;

whereby to determine more accurate values for $\Delta' = \Delta_{J'}$;

whereby it is determined that the phase of the sensor $$\phi' = 2\pi \left( \frac{\Delta_{J'}}{\lambda_1} + k_1 \right)$$

and $$\Delta' = \Delta_{J'} + k_1 \lambda_1$$

where $k_1$ is an integer such that $|k_1| \leq K$ $$\bar{\lambda}_1 = \frac{1}{n_1} \sum_{i=1}^{n_1} \lambda_{1i}$$

j'=the index such that (a) $V_1(j=j')$ is the maximum element in the correlation vector, or, (b) $E_1(j=j')$ is the minimum element in the absolute deviation vector E(j)

G. preforming a second characteristic matrix $S_2(j,i)$, of size r x $n_2$, for the system such that each row j (j=1,2,3 . . . r) is preformed at the same predetermined constant optical path difference $\Delta_j$ as in A. above H. transmitting light from said laser through the system at $n_2$ different laser wavelengths $\lambda_{2i}$ such that;

$$2\pi \Delta_{min} \left( \frac{1}{\lambda_{2l}} - \frac{1}{\lambda_{2n2}} \right) \geq 2\pi$$

where
$\Delta_{min}$=minimum optical path difference of the sensor
i=1,2,3 . . . $n_2$
$\lambda_{2i}$ is indexed so that $\lambda_{2i}$ increases in magnitude as i increases in magnitude
each element of the characteristic matrix is expressed as $$S_2(j,i) = A\left(1 + C\cos\frac{2\pi\Delta_j}{\lambda_{2i}}\right)$$

where
A and C are constants related to the throughput and the contrast of the sensor at the wavelength of the corresponding laser;
I. obtaining a different datum at each wavelength $\lambda_{2i}$ whereby to obtain a set of $n_2$ different data;
J. forming a vector $D_2(i)$ from said $n_2$ different data; where $$D_2(i) = A2\left(1 + C_2\cos\frac{2\pi\Delta''}{\lambda_{2i}}\right)$$

and then either
K1. multiplying said characteristic matrix by said vector to obtain a correlation vector $V_2(j)$;
L1. determining which element of the vector $V_2(j)$ has the largest magnitude, $V_2(j=j'')$; or
K2. dividing said vector by each row of said characteristic matrix to obtain a second matrix $A_2(j,i)$;
L2. forming an absolute deviation vector $E_2(j)$ using the relationship:

$$E_2(j) = \frac{\sum_{i}^{\bar{n}_2} \left| A_2(j,i) - \frac{1}{\bar{n}_2} \sum_{i}^{\bar{n}_2} A_2(j,i) \right|}{\sum_{i}^{\bar{n}_2} A_2(j,i)}$$

wherein
$\bar{n}_2$=number of readings in the data set which satisfy the condition:

$$|S_2(j,i) - A| = \left| AC\cos\frac{2\pi\Delta_j}{\lambda_i} \right| < a_{th}AC$$

wherein
$a_{th}$ is a threshold value such that $0 < a_{th} < 1$;
L2.1 determining which element of the vector $E_2(j)$ has the smallest magnitude, $E_2(j=j'')$; or
k1. multiplying said characteristic matrix by said vector to obtain a correlation vector $V_2(j)$;
L1. determining which element of the vector $V_2(j)$ has the largest magnitude, $V_2(j=J'')$;
to determine approximate values for $\Delta''$ and $\Delta_{j''}$ and then:
K2. dividing each vector by each row, within the neighbourhood of J'' such that $J''-r'' \leq j \leq J''+r''$, where $r'' \leq r$, of said characteristic matrix to obtain a second matrix $A_2(j,i)$;
L2. forming an absolute deviation vector $E_2(j)$ using the relationship:

$$E_2(j) = \frac{\sum_{i}^{\bar{n}_2} \left| A_2(j,i) - \frac{1}{\bar{n}_2} \sum_{i}^{\bar{n}_2} A_2(j,i) \right|}{\sum_{i}^{\bar{n}_2} A_2(j,i)}$$

wherein
$\bar{n}_2$=number of readings in the data set which satisfy the condition:

$$|S_2(j,i) - A| = \left| AC\cos\frac{2\pi\Delta_j}{\lambda_{2i}} \right| a_{th}AC$$

wherein
$a_{th}$ is a threshold value such that $0 < a_{th} < 1$;
L2.1 determining which element of the vector $E_2(j)$ has the smallest magnitude, $E_2(j=j'')$;
whereby to determine more accurate value for $\Delta'' = \Delta_{j''}$;
whereby it is determined that the phase of the sensor $$\phi'' = 2\pi\left(\frac{\Delta_{j''}}{\lambda_2} + k_2\right)$$

and $$\Delta'' = \Delta_{j''} + k_2\bar{\lambda}_2$$

where
$k_2$ is an integer such that $|k_2| \leq K$ $$\bar{\lambda}_2 = \frac{1}{n_2} \sum_{i=1}^{n_2} \lambda_{2i}$$

j''=the index such that (a) $V_2(j=j'')$ is the maximum element in the correlation vector, or, (b) $E_2(j=j'')$ is the minimum element in the absolute deviation vector $E_2(j)$
determining $k_1$ or $k_2$ by determining the minimum $|\Delta' - \Delta''|$ among all possible values of $k_1$ and $k_2$;
whereby to obtain the optical path difference $$\Delta = \Delta_{j'} + k_1\overline{\lambda}_1 = \Delta_{j'} + k_2\overline{\lambda}_2.$$

10. A method as defined in claim 9 wherein said system comprises means for detecting output light intensity $I_1(\lambda_{li})$ and $I_2(\lambda_{2i})$ of said interferometer at each of said wavelengths; and means for detecting the gain ($G_1(\lambda_{li})$) and $G_2(\lambda_{2i})$ of said lasers at each of said wavelengths;

determining the ratio $$\frac{I_1(\lambda_{1i})}{G_1(\lambda_{1i})}$$

wherein $$D_1(i) = \frac{I_1(\lambda_{1i})}{G_1(\lambda_{1i})}$$

and the further step of determining the ratio $$\frac{I_2(\lambda_{2i})}{G_2(\lambda_{2i})}$$

wherein $$D_2(i) = \frac{I_2(\lambda_{2i})}{G_2(\lambda_{2i})}.$$

11. A method as defined in claim 10 wherein said characteristic matrices $S_1(j,i)$ and $S_2(j,i)$ are preformed by:

selected r different optical path differences $\Delta_j$;

setting said interferometer to said optical path differences $\Delta_j$ one at a time;

at each jth optical path difference transmitting light from said lasers through the system at $n_1$ different laser wavelengths $\lambda_{li}$, and at $n_2$ different laser wavelengths $\lambda_{2i}$;

whereby, the magnitude of each element $S_1(j,i)$ and $S_2(j,i)$ are determined by calculating the ratios:

$$S_1(j,i) = \left[\frac{I_1(\lambda_{1i})}{G_1(\lambda_{1i})}\right]_j$$

$$S_2(j,i) = \left[\frac{I_2(\lambda_{2i})}{G_2(\lambda_{2i})}\right]_j.$$

12. A method as defined in claim 11 wherein $r \geq m$; wherein m is an integer; and m is selected such that $\lambda_1/m$ is the fraction of a fringe the system can resolve.

* * * * *

UNITED STATES PATENT AND TRADEMARK OFFICE
CERTIFICATE OF CORRECTION

PATENT NO. : 5,096,296
DATED : March 17, 1992
INVENTORS : Zhuo-Jun Lu

It is certified that error appears in the above-identified patent and that said Letters Patent is hereby corrected as shown below:

Col. 2, line 1, Delete "corelationship" and insert therefore --correlationship--.

Col. 4, line 31, In the equation, delete "$\frac{1}{\lambda_{n1}}$" and insert therefore --$\frac{1}{\lambda_{1n1}}$--.

Col. 5, line 5, In the equation, delete the numerator "$\sum_{i}^{\overline{n_1}} \left| A_1(j,i) - \frac{1}{n_1}\sum_{i}^{\overline{n_1}} A_1(j,i) \right|$" and insert therefore --$\sum_{i}^{\overline{n_1}} \left| A_1(j,i) - \frac{1}{\overline{n_1}}\sum_{i}^{\overline{n_1}} A_1(j,i) \right|$--.

Col. 5, line 36 In the equation, delete the numerator "$\sum_{i}^{\overline{n_1}} \left| A_1(j,i) - \frac{1}{n_1}\sum_{i}^{\overline{n_1}} A_1(j,i) \right|$" and insert therefore --$\sum_{i}^{\overline{n_1}} \left| A_1(j,i) - \frac{1}{\overline{n_1}}\sum_{i}^{\overline{n_1}} A_1(j,i) \right|$--.

UNITED STATES PATENT AND TRADEMARK OFFICE
CERTIFICATE OF CORRECTION

PATENT NO. : 5,096,296
DATED : March 17, 1992
INVENTORS : Zhuo-Jun Lu

It is certified that error appears in the above-identified patent and that said Letters Patent is hereby corrected as shown below:

Col. 6, line 60, In the equation, delete the numerator " $\sum_{i}^{\overline{n_1}} \left| A_1(j,i) - \frac{1}{n_1} \sum_{i}^{\overline{n_1}} A_1(j,i) \right|$ " and insert therefore -- $\sum_{i}^{\overline{n_1}} \left| A_1(j,i) - \frac{1}{\overline{n_1}} \sum_{i}^{\overline{n_1}} A_1(j,i) \right|$ --.

Col. 7, line 17, Delete " $J''-r'' < j < J''+r''$ " and insert therefore

" $J''-r'' \leq j \leq J''+r''$ ".

Col. 7, line 25, In the equation, delete the numerator " $\sum_{i}^{\overline{n_2}} \left| A_2(j,i) - \frac{1}{n_2} \sum_{i}^{\overline{n_2}} A_2(j,i) \right|$ " and insert therefore -- $\sum_{i}^{\overline{n_2}} \left| A_2(j,i) - \frac{1}{\overline{n_2}} \sum_{i}^{\overline{n_2}} A_2(j,i) \right|$ --.

Col. 8, line 66, Delete "mn" and insert therefore --nm--.

Col. 9, line 2, Delete "width" and insert therefore --wide--.

Col. 9, line 6, After "coupler 6", delete "," and insert therefore --.--.

Col. 10, line 59, Delete "an" and insert therefore "and".

UNITED STATES PATENT AND TRADEMARK OFFICE
CERTIFICATE OF CORRECTION

PATENT NO. : 5,096,296

DATED : March 17, 1992

INVENTORS : Zhuo-Jun Lu

It is certified that error appears in the above-identified patent and that said Letters Patent is hereby corrected as shown below:

Col. 11, line 29, Between "such" and "that" delete "as".

Col. 11, line 41, Delete " $\Delta_j = \Delta_0 j \overline{\lambda}/m$ and insert therefore -- $\Delta_j = \Delta_0 + j \dfrac{\overline{\lambda}}{m}$ --.

UNITED STATES PATENT AND TRADEMARK OFFICE
CERTIFICATE OF CORRECTION

PATENT NO. : 5,096,296
DATED : March 17, 1992
INVENTORS : Zhuo-Jun Lu

It is certified that error appears in the above-identified patent and that said Letters Patent is hereby corrected as shown below:

Col. 16, line 24, Delete the equation " $|S(j,i)-A| = \left|ACos\dfrac{2\pi\Delta_j}{\lambda_i}\right| < a_{th}AC$ " and insert therefore -- $|S(j,i)-A| = \left|AC\cos\dfrac{2\pi\Delta_j}{\lambda_i}\right| < a_{th}AC$ --.

Col. 16, line 66, Delete " $\lambda_1$ " and insert therefore -- $\lambda_i$ --.

Col. 18, line 10, Delete " $n_1 =$ " and insert therefore -- $\overline{n_1} =$ --.

Col. 18, line 39, In the equation, delete the numerator " $\sum\limits_{i}^{\overline{n_1}} \left| A(j,i) - \dfrac{1}{\overline{n}} \sum\limits_{i}^{\overline{n_1}} A(j,i) \right|$ " and insert therefore -- $\sum\limits_{i}^{\overline{n_1}} \left| A(j,i) - \dfrac{1}{\overline{n_1}} \sum\limits_{i}^{\overline{n_1}} A(j,i) \right|$ --.

Col. 18, line 43, Delete " $n_1 =$ " and insert therefore -- $\overline{n_1} =$ --.

UNITED STATES PATENT AND TRADEMARK OFFICE
CERTIFICATE OF CORRECTION

PATENT NO. : 5,096,296

DATED : March 17, 1992

INVENTOR(S) : Zhuo-Jun Lu

It is certified that error appears in the above-identified patent and that said Letters Patent is hereby corrected as shown below:

Col. 18, line 65, Delete " $\Delta' = \Delta_j + k_1 \lambda_1$ " and insert therefore -- $\Delta' = \Delta_j + k_1 \overline{\lambda_1}$ --.

Col. 19, line 14, After "above" insert --;--.

Col. 19, line 60, In the equation, delete the numerator " $\sum_{i}^{\overline{n_2}} \left| A_2(j,i) - \frac{1}{n_2} \sum_{i}^{\overline{n_2}} A_2(j,i) \right|$ "

and insert therefore -- $\sum_{i}^{\overline{n_2}} \left| A_2(j,i) - \frac{1}{\overline{n_2}} \sum_{i}^{\overline{n_2}} A_2(j,i) \right|$ --.

UNITED STATES PATENT AND TRADEMARK OFFICE
CERTIFICATE OF CORRECTION

PATENT NO. : 5,096,296
DATED : March 17, 1992
INVENTOR(S) : Zhuo-Jun Lu

It is certified that error appears in the above-identified patent and that said Letters Patent is hereby corrected as shown below:

Col. 20, line 18, Delete " $r'' \leq r$ " and insert therefore -- $r'' < r$ --.

Col. 21, line 10, After "gain", delete the first "(".

Col. 22, line 8, Delete "selected" and insert therefore --selecting--.

Col. 22, line 11, Between "difference" and "transmitting" insert --,--.

Signed and Sealed this

Fifth Day of October, 1993

Attest:

BRUCE LEHMAN

Attesting Officer  Commissioner of Patents and Trademarks